(12) United States Patent
Takenaka et al.

(10) Patent No.: US 11,243,313 B2
(45) Date of Patent: Feb. 8, 2022

(54) RADIATION IMAGE CAPTURING APPARATUS AND RADIATION IMAGE CAPTURING SYSTEM

(71) Applicant: CANON KABUSHIKI KAISHA, Tokyo (JP)

(72) Inventors: Katsuro Takenaka, Honjo (JP); Shoshiro Saruta, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/867,401

(22) Filed: May 5, 2020

(65) Prior Publication Data

US 2020/0264319 A1 Aug. 20, 2020

Related U.S. Application Data

(63) Continuation of application No. PCT/JP2018/040045, filed on Oct. 29, 2018.

(30) Foreign Application Priority Data

Nov. 10, 2017 (JP) .............................. JP2017-217014

(51) Int. Cl.
*G01T 1/20* (2006.01)
*A61B 6/00* (2006.01)

(52) U.S. Cl.
CPC ........ *G01T 1/2002* (2013.01); *G01T 1/20184* (2020.05); *A61B 6/4216* (2013.01); *A61B 6/4233* (2013.01)

(58) Field of Classification Search
CPC ... A61B 6/4216; A61B 6/4233; G01T 1/2002; G01T 1/20181; G01T 1/20184
See application file for complete search history.

(56) References Cited

U.S. PATENT DOCUMENTS

2006/0227933 A1  10/2006  Cantu et al.
2011/0233415 A1* 9/2011  Nakatsugawa ....... G01T 1/2985
                                                          250/370.08
(Continued)

FOREIGN PATENT DOCUMENTS

JP    H07-120557 A    5/1995
JP    2008-516692 A   5/2008
(Continued)

*Primary Examiner* — Mark R Gaworecki
(74) *Attorney, Agent, or Firm* — Canon U.S.A., Inc. IP Division

(57) ABSTRACT

A radiation image capturing apparatus includes a pixel array including conversion elements arranged in rows and columns on an optically transparent substrate, signal lines that outputs a signal generated by the conversion elements and that extends in a column direction, a first scintillator disposed near a first surface of the substrate, and a second scintillator disposed near a second surface of the substrate opposite the first surface. The conversion elements include first conversion elements and second conversion elements. A light shielding layer is disposed between the first scintillator and the second conversion elements such that an amount of light that is received by the second conversion elements from the first scintillator is smaller than that received by the first conversion elements. A number of columns of the conversion elements is equal to a number of the signal lines.

20 Claims, 14 Drawing Sheets

(56) References Cited

U.S. PATENT DOCUMENTS

| | | | |
|---|---|---|---|
| 2013/0082184 A1 | 4/2013 | Nakatsugawa et al. | |
| 2013/0126743 A1 | 5/2013 | Iwakiri et al. | |
| 2017/0097425 A1* | 4/2017 | Shedlock | G01T 1/2018 |
| 2018/0226168 A1 | 8/2018 | Proksa | |
| 2019/0353802 A1* | 11/2019 | Steinhauser | G01T 1/20187 |

FOREIGN PATENT DOCUMENTS

| | | |
|---|---|---|
| JP | 2010-56396 A | 3/2010 |
| JP | 2012-26932 A | 2/2012 |
| JP | 2012-112928 A | 6/2012 |
| JP | 2012-233781 A | 11/2012 |
| JP | 2016-156719 A | 9/2016 |
| WO | 2017/013153 A1 | 1/2017 |

\* cited by examiner

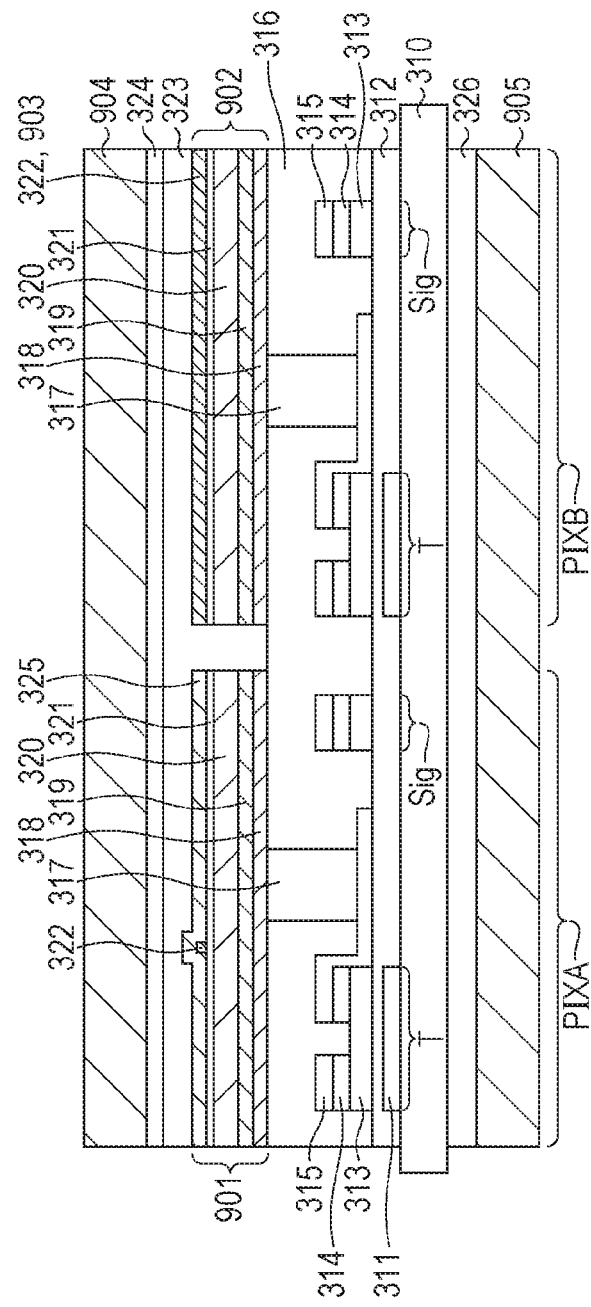

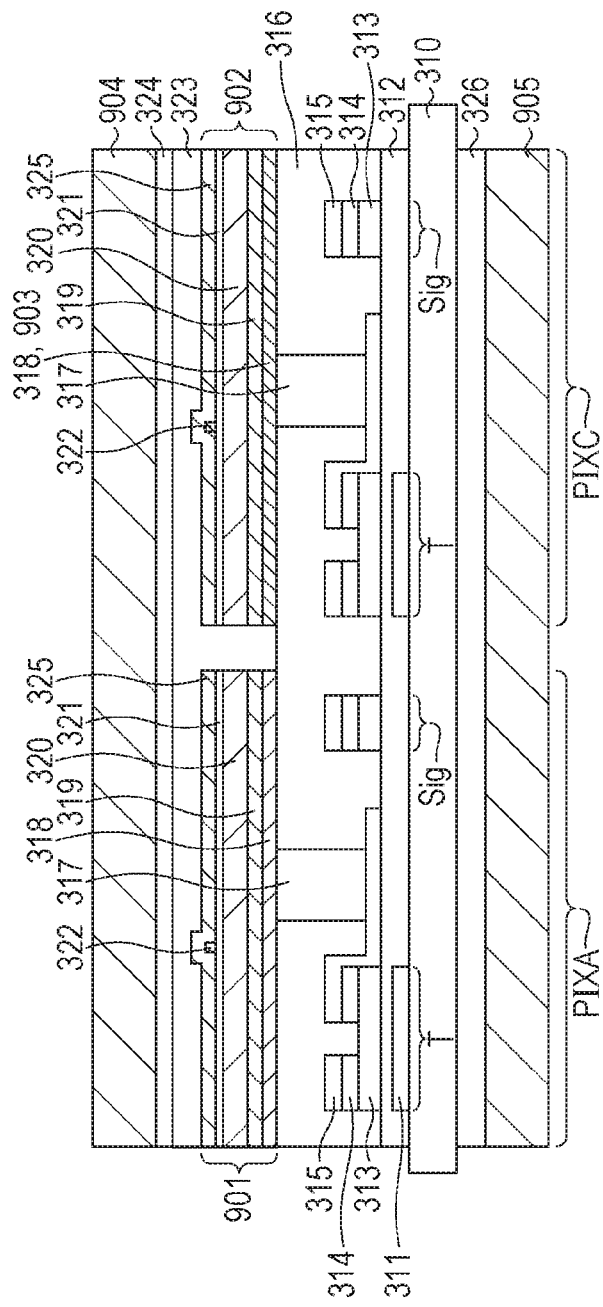

901　902

901　902

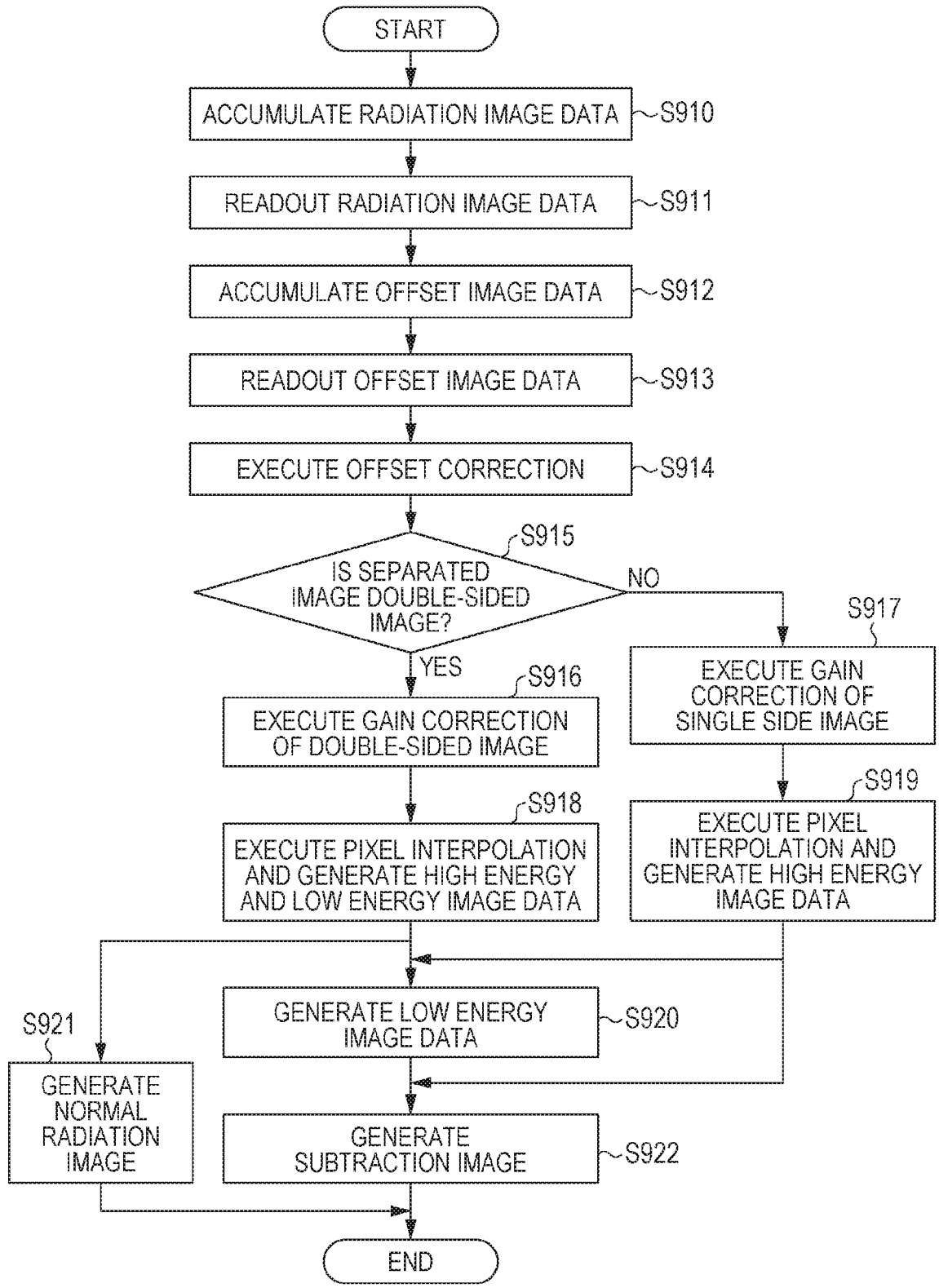

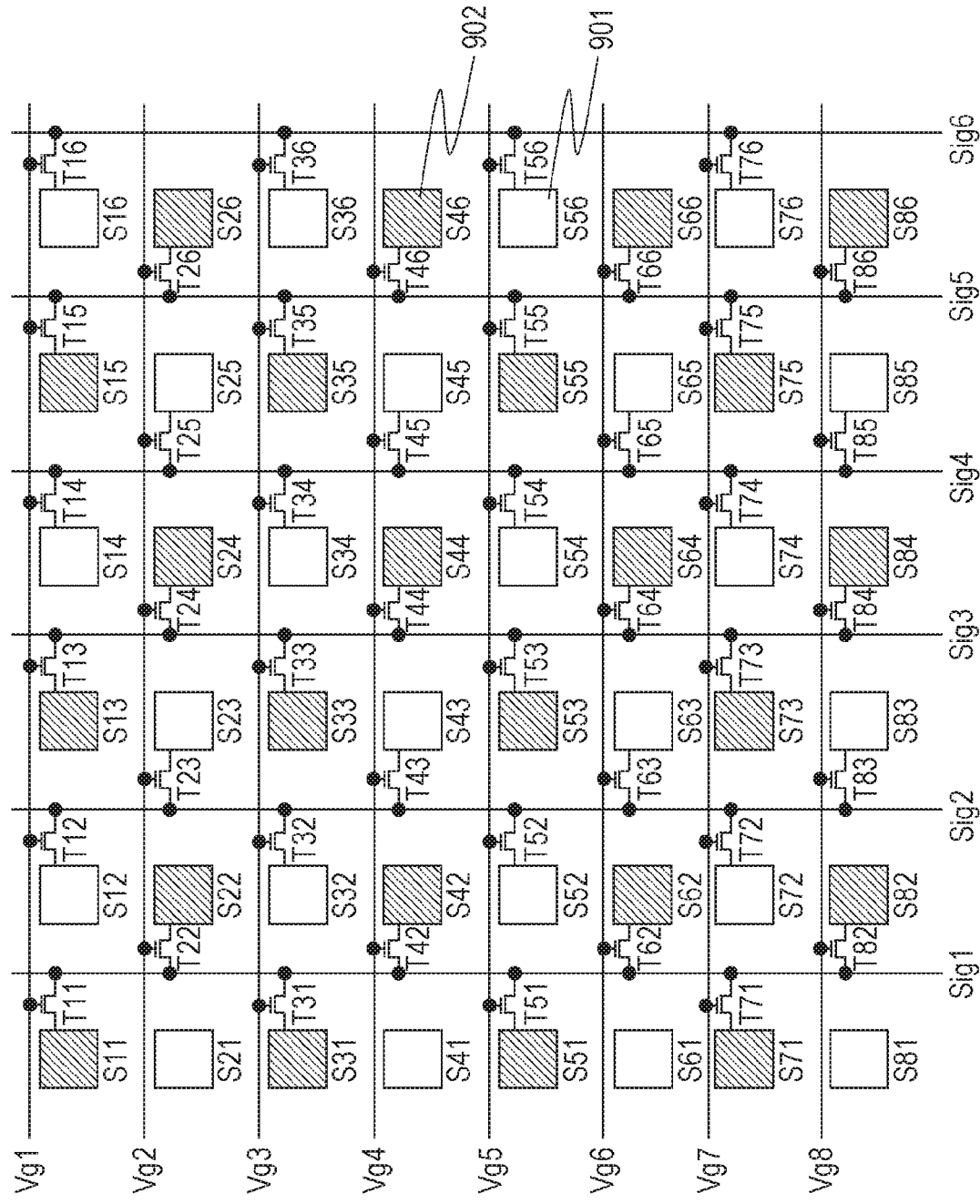

RADIATION IMAGE CAPTURING APPARATUS AND RADIATION IMAGE CAPTURING SYSTEM

CROSS-REFERENCE TO RELATED APPLICATIONS

This application is a Continuation of International Patent Application No. PCT/JP2018/040045, filed Oct. 29, 2018, which claims the benefit of Japanese Patent Application No. 2017-217014, filed Nov. 10, 2017, both of which are hereby incorporated by reference herein in their entirety.

BACKGROUND OF THE INVENTION

Field of the Invention

The present invention relates to a radiation image capturing apparatus and a radiation image capturing system.

Description of the Related Art

A radiation image capturing apparatus that is widely used as an image capturing apparatus for use in medical image diagnosis or nondestructive inspection includes an image capturing panel that includes arrayed pixels each of which includes a combination of a conversion element that converts radiation into an electric charge and a switch element such as a thin film transistor (TFT). It is known that the radiation image capturing apparatus is used to acquire radiation images of radiation having different energy components, and that an energy subtraction image is acquired by separating or emphasizing a specific part of a subject from a difference between the acquired radiation images. Japanese Patent Application Laid-Open No. 2010-56396 discloses that scintillators are disposed on both surfaces of an optically transparent substrate, a photodiode detects light that is emitted from one of the scintillators, and a photodiode detects light that is emitted from the other scintillator. Signals of two different energy components are acquired by one-time emission of radiation from the photodiodes that detect the light that is emitted from the different scintillators via respective signal wiring lines, and an energy subtraction image can be generated.

According to Japanese Patent Application Laid-Open No. 2010-56396, the two signal wiring lines that are associated with the two photodiodes are used to generate a piece of pixel data of the radiation images. Accordingly, the wiring structure of the image capturing panel and a circuit for reading signals from the signal wiring lines are complex, and there is a possibility that manufacturing costs and apparatus costs increase.

SUMMARY OF THE INVENTION

It is an object of the present invention to provide a radiation image capturing apparatus that can acquire an energy subtraction image with a simple structure.

In view of the above circumstances, a radiation image capturing apparatus according to an embodiment of the present invention includes a pixel array including a plurality of conversion elements arranged in a plurality of rows and a plurality of columns on an optically transparent substrate, a plurality of signal lines that outputs a signal generated by the plurality of conversion elements and that extends in a column direction, a first scintillator disposed near a first surface of the substrate, and a second scintillator disposed near a second surface of the substrate opposite the first surface. The plurality of conversion elements includes a plurality of first conversion elements and a plurality of second conversion elements. A light shielding layer is disposed between the first scintillator and the plurality of second conversion elements such that an amount of light that is received by the plurality of second conversion elements from the first scintillator is smaller than that received by the plurality of first conversion elements. A number of columns of the plurality of conversion elements is equal to a number of the plurality of signal lines.

Further features of the present invention will become apparent from the following description of exemplary embodiments with reference to the attached drawings.

BRIEF DESCRIPTION OF THE DRAWINGS

FIG. 3A illustrates an example of a sectional pixel structure of the radiation image capturing apparatus in FIG. 1.
FIG. 3B illustrates an example of a sectional pixel structure of the radiation image capturing apparatus in FIG. 1.
FIG. 7 illustrates the operation flow of the radiation image capturing apparatus in FIG. 1.
FIG. 9 illustrates an example of the structure of the image capturing panel of the radiation image capturing apparatus in FIG. 1.

DESCRIPTION OF THE EMBODIMENTS

Figure 1:
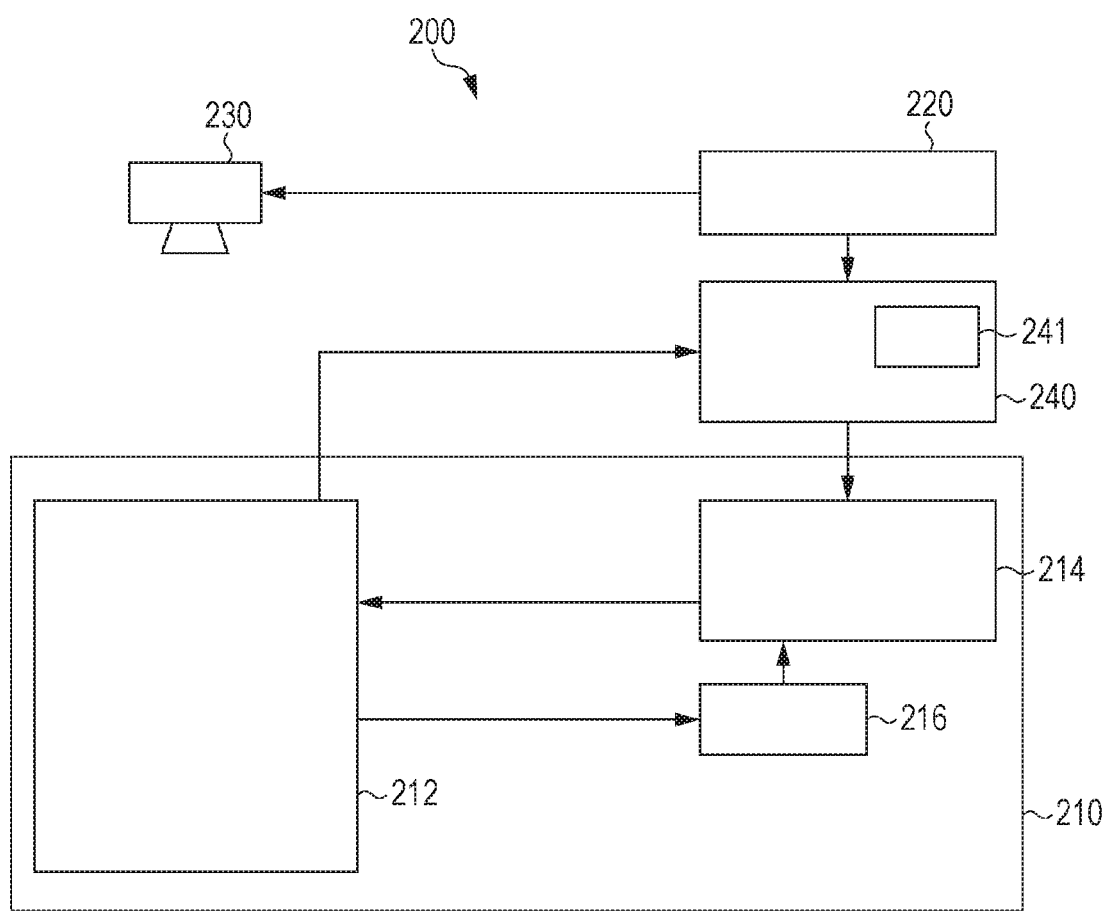
FIG. 1 illustrates an example of the structure of a radiation image capturing system that includes a radiation image capturing apparatus according to an embodiment of the present invention.

A radiation image capturing apparatus according to a specific embodiment of the present invention will hereinafter be described with reference to the attached drawings. In the following description and the drawings, common components in the drawings are designated by common reference characters. Accordingly, the drawings are mutually referred to describe the common components, and a description of the components that are designated by the common reference characters is appropriately omitted. According to the present invention, radiation can include an α-ray, a β-ray, and a γ-ray, which are beams that are produced by particles (including photons) that are emitted due to radioactive decay, and a beam having the same degree of energy or more such as an X-ray, a particle beam, and a cosmic ray.

The structure and operation of the radiation image capturing apparatus according to the embodiment of the present invention will be described with reference to FIG. 1 to FIG. 8B. FIG. 1 illustrates an example of the structure of a radiation image capturing system 200 that includes a radiation image capturing apparatus 210 according to the embodiment of the present invention. The radiation image capturing system 200 electrically captures an optical image that is converted from radiation and acquires an electrical signal (radiation image data) for generating a radiation image. The radiation image capturing system 200 includes, for example, the radiation image capturing apparatus 210, a radiation source 230, an exposure control unit 220, and a computer 240.

The radiation source 230 starts emitting radiation in accordance with an exposure instruction (radiation instruction) from the exposure control unit 220. The radiation that is emitted from the radiation source 230 passes through a subject, not illustrated, and the radiation image capturing apparatus 210 is irradiated with the radiation. The radiation source 230 stops emitting the radiation in accordance with a stop instruction from the exposure control unit 220.

The radiation image capturing apparatus 210 includes an image capturing panel 212 and a control unit 214 that controls the image capturing panel 212. The control unit 214 generates a stop signal for stopping emission of the radiation from the radiation source 230, based on a signal that is acquired from the image capturing panel 212. The stop signal is supplied to the exposure control unit 220. The exposure control unit 220 transmits the stop instruction to the radiation source 230 in response to the stop signal. The control unit 214 can include, for example, a PLD (abbreviation for Programmable Logic Device) such as a FPGA (abbreviation for Field Programmable Gate Array), an ASIC (abbreviation for Application Specific Integrated Circuit), a general-purpose computer that incorporates a program, or a combination of all or a part of these.

The computer 240 controls the radiation image capturing apparatus 210 and the exposure control unit 220. The computer 240 receives radiation image data that is outputted from the radiation image capturing apparatus 210 and includes a signal processing unit 241 that processes the radiation image data. The signal processing unit 241 can generate a radiation image from the radiation image data.

The exposure control unit 220 includes, for example, an exposure switch (not illustrated). When a user turns on the exposure switch, the exposure control unit 220 transmits the exposure instruction to the radiation source 230 and transmits a start notification that represents the start of emission of radiation to the computer 240. The computer 240 that receives the start notification reports the start of emission of radiation to the control unit 214 of the radiation image capturing apparatus 210 in response to the start notification.

Figure 2:
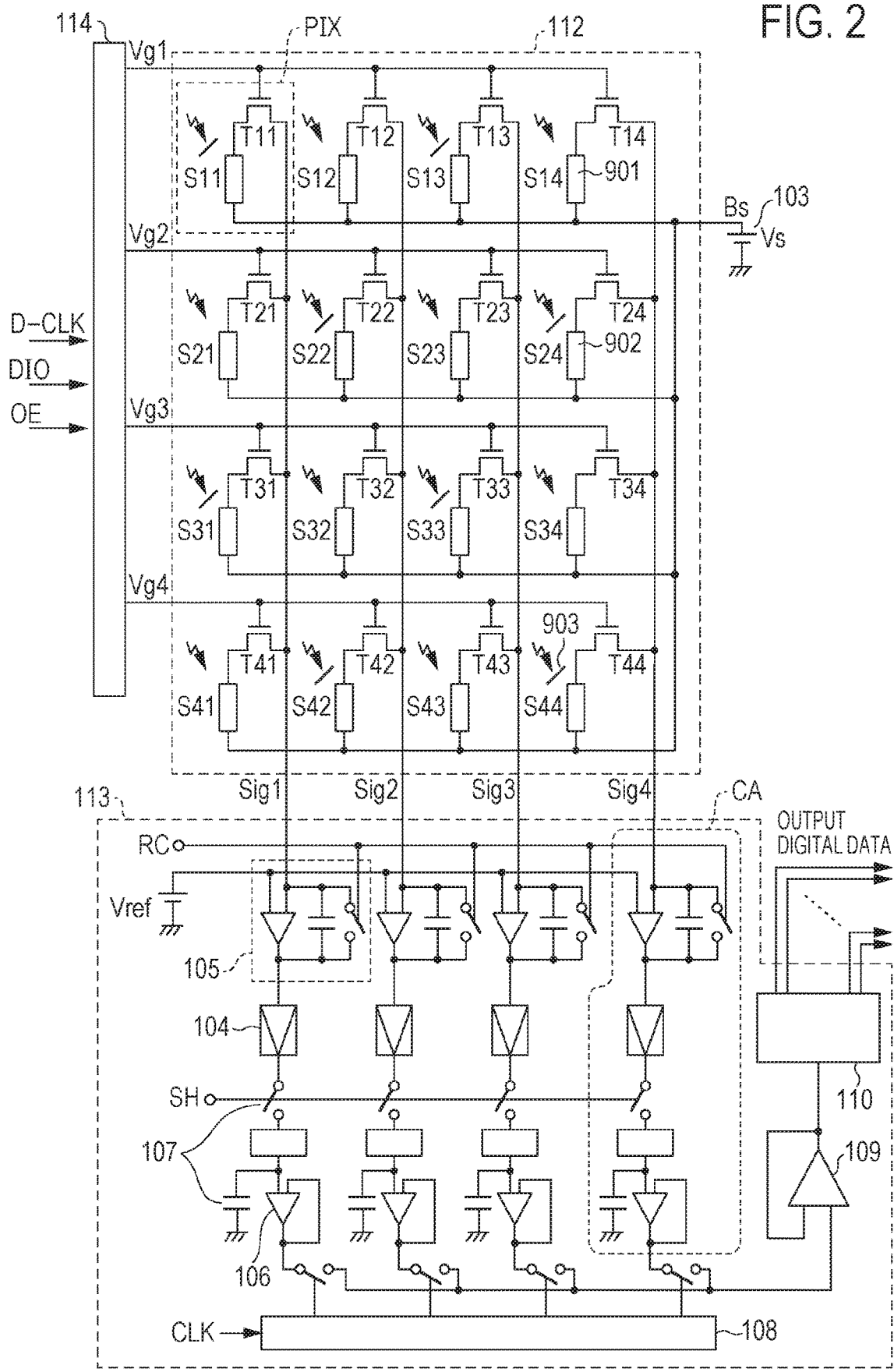
FIG. 2 illustrates an example of the structure of an image capturing panel of the radiation image capturing apparatus in FIG. 1.

FIG. 2 illustrates an example of the structure of the image capturing panel 212. The image capturing panel 212 includes a pixel array 112. The pixel array 112 includes pixels PIX that include respective conversion elements S that are arrayed in a two-dimensional array for detecting the radiation. The pixel array 112 also includes column signal lines Sig1 to Sig4 that extend in a column direction (the vertical direction in FIG. 2) for outputting signals that are generated by the conversion elements S. The image capturing panel 212 also includes a drive circuit (row-selecting circuit) 114 that drives the pixel array 112, and a readout circuit 113 that detects the signals that appear in the column signal lines Sig of the pixel array 112. In the structure illustrated in FIG. 2, the pixel array 112 includes the pixels PIX in 4 rows×4 columns for simplicity of illustration. However, a larger number of the pixels PIX can be actually arrayed. In an example, the image capturing panel 212 can have a dimension of 17 inches and can include the pixels PIX in about 3000 rows×about 3000 columns. That is, the conversion elements S are arranged in rows and columns.

Each pixel PIX includes the conversion element S that detects the radiation, and a switch T that connects the conversion element S and a column signal line Sig (the signal line Sig associated with the conversion element C among the signal lines Sig). The conversion element S outputs a signal corresponding to the amount of incident radiation to the column signal line Sig. An example of the conversion element S may be a MIS photodiode that is disposed on an insulating substrate such as a glass substrate and that is mainly composed of amorphous silicon. The conversion element S may be a PIN photodiode. According to the present embodiment, the conversion element S can be an indirect element that converts the radiation into light by using a scintillator and subsequently detects the light. The scintillator of the indirect element can be shared with the pixels PIX (the conversion elements S).

The switch T can be constituted of, for example, a transistor such as a thin film transistor (TFT) that includes a control terminal (gate) and two main terminals (source and drain). The conversion element S includes two main electrodes. One of the main electrodes of the conversion element S is connected to one of the two main terminals of the switch T. The other main electrode of the conversion element S is connected to a bias power supply 103 with a common bias line Bs interposed therebetween. The bias power supply 103 supplies a bias voltage Vs. The control terminal of the switch T of each pixel PIX that is arranged in a first row is connected to a gate line Vg1 that extends in a row direction (the horizontal direction in FIG. 2). Similarly, the control terminals of switches SW of the pixels PIX that are arranged in second to fourth rows are connected to the gate lines Vg2 to Vg4. The drive circuit 114 supplies a gate signal to the gate lines Vg1 to Vg4.

In each pixel PIX that is arranged in a first column, the main terminal of the switch T that is not connected to the conversion element S is connected to the column signal line Sig1 in the first column. Similarly, in the pixels PIX that are arranged in second to fourth columns, the main terminals of the switches T that are not connected to the conversion elements S are connected to the column signal lines Sig2 to Sig4 in the second to fourth columns.

The readout circuit 113 includes column amplifier units CA that are associated with the respective column signal lines Sig. Each column amplifier unit CA can include an integrator amplifier 105, a variable amplifier 104, a sample hold circuit 107, and a buffer circuit 106. The integrator amplifier 105 amplifies a signal that appears in the column signal line Sig. The integrator amplifier 105 can include an operational amplifier, an integral capacity that is connected in parallel between an inverting input terminal and an output terminal of the operational amplifier, and a reset switch. A reference electric potential Vref is supplied to a non-inverting input terminal of the operational amplifier. The integral capacity is reset, and the electric potential of the column signal line Sig is reset to the reference electric potential Vref by turning on the reset switch. The reset switch can be controlled by a reset pulse RC that is supplied from the control unit 214.

The variable amplifier 104 amplifies a signal that is outputted from the integrator amplifier 105 at a predetermined amplification factor. The sample hold circuit 107 samples and holds a signal that is outputted from the variable amplifier 104. The sample hold circuit 107 can include a sampling switch and a sampling capacity. The buffer circuit 106 buffers (impedance conversion) a signal that is outputted from the sample hold circuit 107 and outputs the signal. The sampling switch can be controlled by a sampling pulse that is supplied from the control unit 214.

The readout circuit 113 also includes a multiplexer 108 that selectively outputs signals from the column amplifier units CA that are associated with the respective column signal lines Sig, in a predetermined order. The multiplexer 108 includes, for example, a shift resistor. The shift resistor performs a shift operation based on a clock signal CLK that is supplied from the control unit 214. The shift resistor selects a single signal from the signals from the column amplifier units CA. The readout circuit 113 can also include a buffer 109 for buffering (impedance conversion) a signal that is outputted from the multiplexer 108, and an AD convertor 110 that converts an analog signal that is outputted from the buffer 109 into a digital signal. The output of the AD convertor 110, that is, radiation image data is transferred to the computer 240.

According to the present embodiment, scintillators that convert the radiation into visible light are disposed near an entrance surface of a substrate on which the radiation is incident and near a back surface opposite the entrance surface so as to cover the respective surfaces. The conversion elements S that are included in the pixels PIX include two kinds of conversion elements S. In the structure illustrated in FIG. 2, conversion elements S12, S14, S21, S23, S32, S34, S41, and S43 receive light from the two scintillators. In the following description, the conversion elements that receive the light from the two scintillators among the conversion elements S are referred to as first conversion elements 901 when specified. On conversion elements S11, S13, S22, S24, S31, S33, S42, and S44, light shielding layers 903 are disposed between one of the scintillators and the conversion elements S. Consequently, the conversion elements S11, S13, S22, S24, S31, S33, S42, and S44 can be shielded from the light from the one of the scintillators and can receive the light from the other scintillator. In the following description, the conversion elements that are shielded from the light from the one of the scintillators among the conversion elements S are referred to as second conversion elements 902 when specified. The light shielding layers 903, which block light that is emitted from a scintillator, may shield light between the scintillator that covers the entrance surface or the back surface of the substrate and the second conversion elements 902. At this time, the second conversion elements 902 may not be completely shielded from the light from the one of the scintillators, provided that the light shielding layers 903 are disposed between the scintillator that covers the entrance surface or the back surface of the substrate and the second conversion elements 902 such that the amount of light that can be received from the one of the scintillators is smaller than that in the case of the first conversion elements 901.

Here, the light shielding layers 903 are disposed between the scintillator near the entrance surface of the substrate and the second conversion elements 902. A low-energy component of the radiation entering from the entrance surface of the substrate is absorbed by the scintillator that covers the entrance surface of the substrate, is converted into visible light, and is incident on the pixels PIX. Since the second conversion elements 902 are shielded from light from the entrance surface of the substrate, light that is emitted from the entrance surface of the substrate is not incident thereon. Accordingly, light that is converted from the low-energy component of the radiation is not incident on the second conversion elements 902. Light that is converted from the low-energy component of the radiation is incident on the first conversion elements 901 because the light shielding layers 903 are not disposed thereon.

A high-energy component of the radiation that is not absorbed by the scintillator that is disposed near the entrance surface of the substrate is absorbed by the scintillator that covers the back surface of the substrate and is converted into visible light. The first conversion elements 901 and the second conversion elements 902 are not shielded from light from the back surface of the substrate, and light that is converted from the high-energy component of the radiation is incident on both of the first conversion elements 901 and the second conversion elements 902.

The first conversion elements 901 can thus acquire a signal attributable to the high-energy component and the low-energy component of the radiation. The second conversion elements 902 can thus acquire a signal attributable to the high-energy component of the radiation. That is, the pixels PIX adjacent to each other can retain information about different radiation energy. Since the pixels PIX adjacent to each other thus retain information that is acquired from the radiation having different energy components, energy subtraction can be performed by using a method described later. The signals of the first conversion elements 901 and the signals of the second conversion elements 902 are read out by using the column signal lines Sig the number of which is equal to the number of the columns of the pixels PIX (and the conversion elements) of the pixel array 112. This enables the radiation image capturing apparatus to acquire an energy subtraction image with a simple structure and prevents the number of the column signal lines from being uselessly increased.

FIG. 3A and FIG. 3B schematically illustrate examples of a sectional structure of a pixel PIXA that includes the first conversion element 901 and a pixel PIXB and a pixel PIXC that each include the second conversion element 902. In a description herein, the radiation enters from an upper part of the figure. However, the radiation may enter from a lower part of the figure. In FIG. 3A, the first conversion element 901 and the second conversion element 902 are disposed between a substrate 310 and a scintillator 904 that is disposed near the entrance surface of the substrate 310. In the pixel PIXB illustrated in FIG. 3A, the light shielding layer 903 is disposed between the second conversion element 902 and the scintillator 904. In FIG. 3B, the first conversion element 901 and the second conversion element 902 are disposed between the substrate 310 and the scintillator 904 that covers the entrance surface of the substrate 310 as in FIG. 3A. In the pixel PIXC in a structure in FIG. 3B, the light shielding layer 903 is disposed between the second conversion element 902 and a scintillator 905 that is disposed near the back surface of the substrate 310 opposite the entrance surface.

The conversion element S of each pixel PIX is disposed above the insulating substrate 310 such as a glass substrate optically transparent to light that is emitted from the scintillators 904 and 905. The pixel PIX includes a conductive layer 311, an insulating layer 312, a semiconductor layer 313, an extrinsic semiconductor layer 314, and a conductive layer 315 that are disposed in this order on the substrate 310. The conductive layer 311 constitutes a gate electrode of the transistor (for example, a TFT) that constitutes the switch T. The insulating layer 312 covers the conductive layer 311. The semiconductor layer 313 is disposed above a part of the conductive layer 311 constituting the gate electrode with the insulating layer 312 interposed therebetween. The extrinsic semiconductor layer 314 is disposed on the semiconductor layer 313 and constitutes the two main terminals (source and drain) of the transistor that constitutes the switch T. The conductive layer 315 constitutes a wiring line pattern that is connected to the two main terminals (source and drain) of the transistor that constitutes the switch T. A part of the conductive layer 315 constitutes the column signal line Sig, and the other part constitutes a wiring line pattern that connects the conversion element S and the switch T to each other.

Each pixel PIX also includes an interlayer insulating layer 316 that convers the insulating layer 312 and the conductive layer 315. In the interlayer insulating layer 316, a contact plug 317 for connection to a part of the conductive layer 315 that constitutes the switch T is disposed. The pixel PIX also includes the conversion element S that is disposed on the interlayer insulating layer 316. In examples illustrated in FIG. 3A and FIG. 3B, each conversion element S is constituted as an indirect conversion element that converts, into an electrical signal, light that is converted from the radiation by the scintillators 904 and 905. The conversion element S includes a conductive layer 318, an insulating layer 319, a semiconductor layer 320, an extrinsic semiconductor layer 321, a conductive layer 322, and an electrode layer 325 that are stacked on the interlayer insulating layer 316. A protective layer 323 and an adhesive layer 324 are disposed on the conversion element S. The scintillator 904 is disposed on the adhesive layer 324 and covers the entrance surface of the substrate 310. The scintillator 905 covers the back surface of the substrate 310 opposite the entrance surface.

The conductive layer 318 constitutes a lower electrode of the conversion element S. The conductive layer 322 and the electrode layer 325 constitute an upper electrode of the conversion element S. The conductive layer 318, the insulating layer 319, the semiconductor layer 320, the extrinsic semiconductor layer 321, and the conductive layer 322 constitute a MIS sensor as the conversion element S. An example of the extrinsic semiconductor layer 321 is an n-type extrinsic semiconductor layer.

The scintillators 904 and 905 can be composed of a GOS (gadolinium oxysulfide) or CsI (cesium iodide) material. The material can be formed by bonding, printing, or depositing. The scintillator 904 and the scintillator 905 may be composed of the same material or may be composed of different materials depending on the energy of the radiation to be acquired.

In an example described according to the present embodiment, each conversion element S is a MIS sensor but is not limited thereto. The conversion element S may be, for example, a pn or PIN photodiode.

The arrangement of the light shielding layer 903 that is disposed on each second conversion element 902 and that shields light entering from the scintillator 904 or the scintillator 905 will now be described. In a structure illustrated in FIG. 3A, the second conversion element 902 of the pixel PIXB includes the conductive layer 318 that constitutes the lower electrode, the semiconductor layer 320, and the conductive layer 322 that constitutes the upper electrode in this order in a direction from the entrance surface of the substrate 310 toward the scintillator 904. The conductive layer 322 that constitutes the upper electrode functions as the light shielding layer 903. Specifically, the conductive layer 322 is composed of a material such as Al, Mo, Cr, or Cu that is opaque to light that is emitted from the scintillator 904, and the conductive layer 322 functions as the light shielding layer 903. That is, the light shielding layer 903 is disposed between the scintillator 904 and the second conversion element 902 such that the amount of light that can be received by the second conversion element 902 of the pixel PIXB from the scintillator 904 is smaller than that received by the first conversion element 901. The second conversion element 902 of the pixel PIXB receives light from the scintillator 905 as in the first conversion element 901 of the pixel PIXA. In FIG. 3B, the second conversion element 902 of the pixel PIXC includes the conductive layer 318 that constitutes the lower electrode, the semiconductor layer 320, the conductive layer 322 that constitutes the upper electrode, and the electrode layer 325 in this order in the direction from the entrance surface of the substrate 310 toward the scintillator 904. The conductive layer 318 that constitutes the lower electrode functions as the light shielding layer 903. Specifically, the conductive layer 318 is composed of a material such as Al, Mo, Cr, or Cu that is opaque to light that is emitted from the scintillator 905, and the conductive layer 322 functions as the light shielding layer 903. That is, the light shielding layer 903 is disposed between the scintillator 905 and the second conversion element 902 such that the amount of light that can be received by the second conversion element 902 of the pixel PIXC from the scintillator 905 is smaller than that received by the first conversion element 901. The second conversion element 902 of the pixel PIXC receives light from the scintillator 904 as in the first conversion element 901 of the pixel PIXA.

The conductive layer 318 and the electrode layer 325 in the first conversion element 901 of the pixel PIXA are composed of a material such as an ITO (indium tin oxide) transparent to the light that is emitted from the scintillator 904. This enables signals having different energy components between the pixel PIXA and the pixel PIXB or the pixel PIXC adjacent thereto to be acquired.

In an example described according to the present embodiment, the conductive layer 322 of the pixel PIXB and the conductive layer 318 of the pixel PIXC have a single layer structure but are not limited thereto. For example, in the conductive layer 322 of the pixel PIXB and the conductive layer 318 of the pixel PIXC, a transparent material and an opaque material may be stacked. In this case, the amount of light to be shielded is determined by the area of the opaque material. According to the present embodiment, the conductive layer 322 of the pixel PIXB and the conductive layer 318 of the pixel PIXC function as the light shielding layers 903. However, the arrangement of the light shielding layers 903 is not limited thereto. In the pixel PIXB, for example, the light shielding layer 903 composed of Al, Mo, Cr, or Cu for exclusive use of light entering from the scintillator 904 may be disposed in the protective layer 323. In this case, the electric potential of the light shielding layer 903 may be kept constant.

In the case where the light from the scintillator 905 is shielded as in the pixel PIXC illustrated in FIG. 3B, the positions of the switch T and the column signal line Sig of the pixel PIXA that receives the light from the scintillator 905 may be shifted toward the pixel PIXC. Such arrangement enables the aperture ratio of the first conversion element 901 of the pixel PIXA with respect to the scintillator 905 to be increased.

It is not necessary for the light shielding layers 903 to completely shield the light that is emitted from the scintillator 904 or the scintillator 905 toward the second conversion elements 902 as described above. The energy subtraction can be performed, provided that the amount of light that is received from the scintillator 904 or the scintillator 905 near the light shielding layer 903 changes between the pixel PIXA and the pixel PIXB or the pixel PIXC adjacent thereto. In this case, correction can be executed in a manner in which the percentage of light incident on the second conversion element 902 of the pixel PIXB or the pixel PIXC to light that is received by the first conversion element 901 of the pixel PIXA is investigated in advance, and a differencing process is performed based on the output of the first conversion element 901.

Figure 4A:
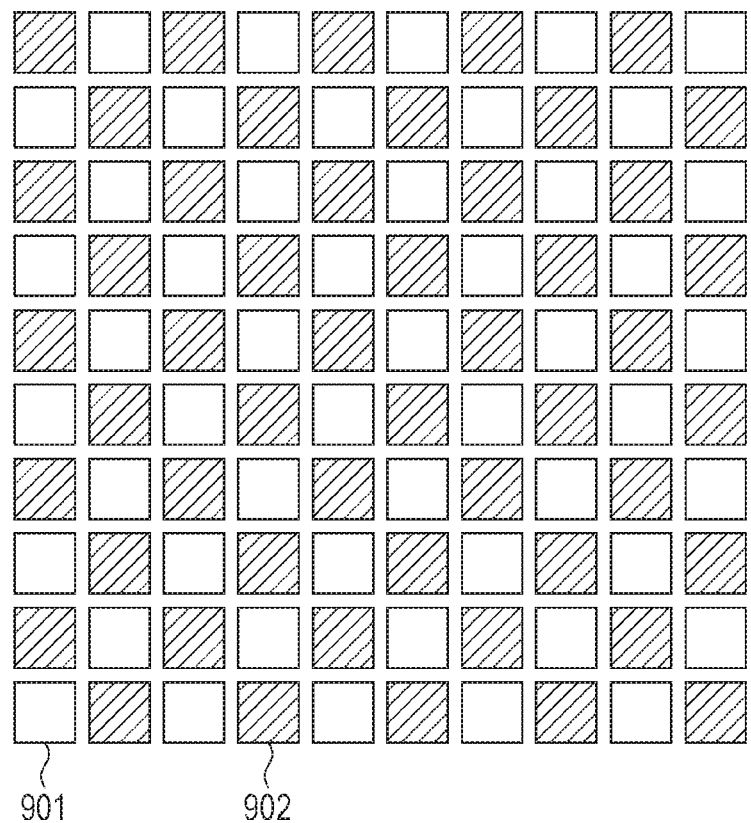
FIG. 4A illustrates an example of arrangement of pixels of the radiation image capturing apparatus in FIG. 1.
Figure 4B:
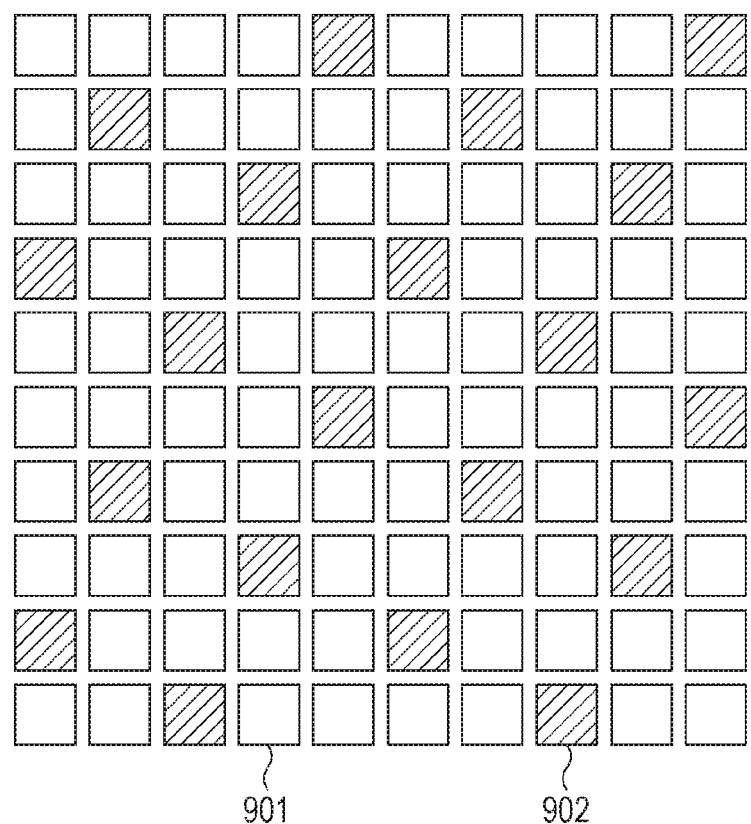
FIG. 4B illustrates an example of arrangement of the pixels of the radiation image capturing apparatus in FIG. 1.

In an orthographic projection on the entrance surface of the substrate 310, as illustrated in FIG. 3A and FIG. 3B, the column signal lines Sig partly overlap the pixels PIX. This structure is advantageous for the point that the area of the conversion element S of each pixel PIX increases but is disadvantageous for the point that capacitive coupling between the column signal lines Sig and the conversion elements S becomes stronger. When the radiation is incident on the conversion elements S, electric charges are accumulated on the conversion elements S, and the electric potential of each conductive layer 318 corresponding to the lower electrode changes, the capacitive coupling between the column signal lines Sig and the conversion elements S causes cross talk in which the electric potential of each column signal line Sig changes. FIG. 4A and FIG. 4B illustrate a measure against the cross talk. Some of the conversion elements S are arranged in the row direction intersecting the column direction such that the same number of the pixels PIX that include the second conversion elements 902 on which the light shielding layers 903 are disposed are arranged in each row. Some of the conversion elements S are arranged in the column direction such that the same number of the pixels PIX that include the second conversion elements 902 are arranged in each column. This arrangement inhibits an artifact from occurring due to the cross talk in each row and each column.

The radiation image capturing apparatus 210 may have a function of automatically detecting the start of emission of the radiation. In this case, for example, each switch T is operated to turn on or off the gate line Vg, a signal from each conversion element S is read out, and the presence or absence of emission of radiation is determined from an output signal. In the case where different numbers of the pixels PIX that include the second conversion elements 902 including the light shielding layer 903 are arranged in each row, the quantities of signals that are outputted in each row differ from each other, and detection precision varies. Accordingly, as illustrated in FIG. 4A and FIG. 4B, some of the conversion elements S are arranged in the row direction intersecting the column direction such that the same number of the pixels PIX that include the second conversion elements 902 on which the light shielding layers 903 are disposed are arranged in each row. This arrangement stabilizes the detection precision with which the start of emission of radiation is automatically detected.

In an example of the arrangement of the pixels PIX in FIG. 4B, the density of the pixels PIX that include the second conversion elements 902 is lower than that in the example of the arrangement of the pixels PIX in FIG. 4A. The light from the scintillator 905 is incident on the conversion elements S via the substrate 310. Accordingly, the light diffuses depending on the thickness of the substrate 310, and a MTF (Modulation Transfer Function) is degraded. For this reason, resolution is not substantially reduced with reduction of the density of the pixels PIX that include the second conversion elements 902. That is, in the case where the second conversion elements 902 receive the light that is emitted from the facing scintillator 905 via the substrate 310, the number of the pixels PIX that include the second conversion elements 902 may be smaller than the number of the pixels PIX that include the first conversion elements 901.

The thickness of the substrate 310 may be decreased by mechanical polishing or chemical polishing to inhibit the light from the scintillator 905 via the substrate 310 from diffusing and to inhibit the MTF from being degraded. To inhibit the MTF from being degraded, as illustrated in FIG. 3A and FIG. 3B, an anti-scattering layer 326 such as a micro-lens or a louver layer for giving directivity to the light that is emitted from the scintillators may be disposed between the scintillator 905 and the substrate 310. To inhibit the MTF from being degraded, the resolution may be increased by a sharpening process in image processing performed by the signal processing unit 241 of the computer 240. To match the MTF between a low-energy component of the light from the scintillator 904 and a high-energy component of the light from the scintillator 905, a higher resolution is matched with a lower resolution to degrade the MTF instead of increasing the resolution. Subsequently, an energy subtraction process may be performed.

Figure 5:
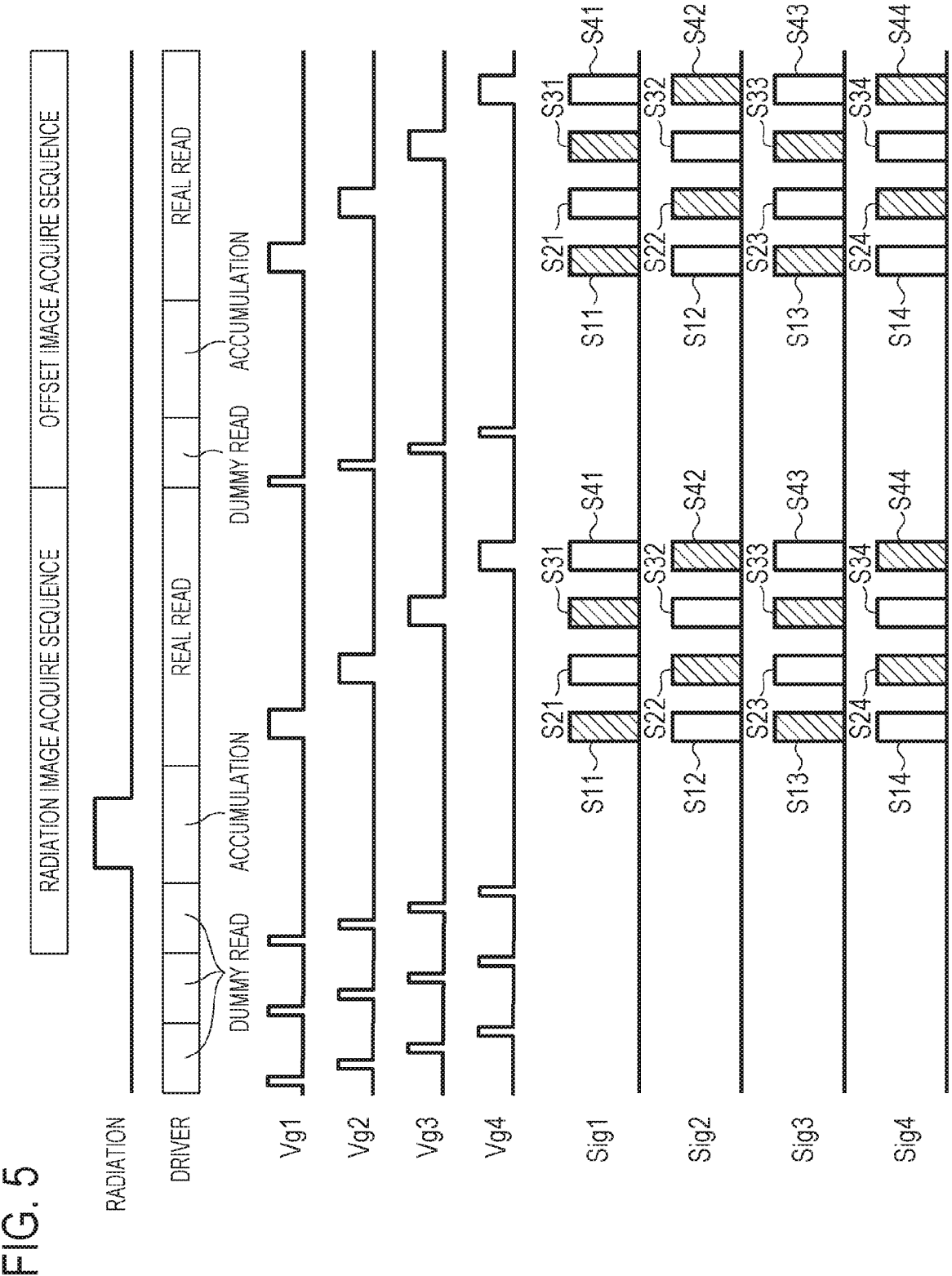
FIG. 5 is a timing chart illustrating the operation of the radiation image capturing apparatus in FIG. 1.

The operation of the radiation image capturing apparatus 210 and the radiation image capturing system 200 will now be described with reference to FIG. 5. In an example of the operation described herein, the radiation image capturing apparatus 210 includes the image capturing panel 212 that includes the pixels PIX that include the conversion elements S and that are arranged in 4 rows and 4 columns as illustrated in FIG. 2. The operation of the radiation image capturing system 200 is controlled by the computer 240. The operation of the radiation image capturing apparatus 210 is controlled by the control unit 214 under control of the computer 240.

The control unit 214 causes the drive circuit 114 and the readout circuit 113 to execute a dummy read until emission of the radiation from the radiation source 230, in other words, emission of the radiation to the radiation image capturing apparatus 210 is started. In the dummy read, gate signals that are supplied to the gate lines Vg1 to Vg4 in the rows of the pixel array 112 are raised to active levels in order by drive of the drive circuit 114 to reset dark electric charges that are accumulated on the conversion elements S. During the dummy read, a reset pulse at an active level is supplied to the reset switch of the integrator amplifier 105, and the column signal lines Sig are reset to have a reference electric potential. The dark electric charge means an electric charge that is produced although no radiation is incident on the conversion elements S.

The control unit 214 can recognize the start of emission of the radiation from the radiation source 230, for example, based on the start notification that is supplied from the exposure control unit 220 via the computer 240. As illustrated in FIG. 1, the radiation image capturing apparatus 210 may include a detection circuit 216 that detects electric current that passes through the bias line Bs or the column signal lines Sig of the pixel array 112. The control unit 214 can recognize the start of emission of the radiation from the radiation source 230, based on the output of the detection circuit 216.

When the radiation is emitted, the control unit 214 controls the switches T such that the switches T are opened (turned off). Consequently, electric charges are produced and accumulated on the conversion elements S by the emitted radiation. The control unit 214 waits in this state until the emission of the radiation ends.

The control unit 214 subsequently causes the drive circuit 114 and the readout circuit 113 to execute a real read. In the real read, gate signals that are supplied to the gate lines Vg1 to Vg4 in the rows of the pixel array 112 are raised to active levels by drive of the drive circuit 114. The readout circuit 113 reads out the electric charges that are accumulated on the conversion elements S via the column signal lines Sig and outputs the electric charges as radiation image data to the computer 240 via the multiplexer 108, the buffer 109, and the AD convertor 110.

Acquisition of offset image data will now be described. The dark electric charges are continuously accumulated on the conversion elements S even while no radiation is emitted. For this reason, the control unit 214 performs the same operation as when the radiation image data is acquired without emission of radiation to acquire the offset image data. An offset component due to the dark electric charges can be removed by subtracting the offset image data from the radiation image data.

Figure 6:
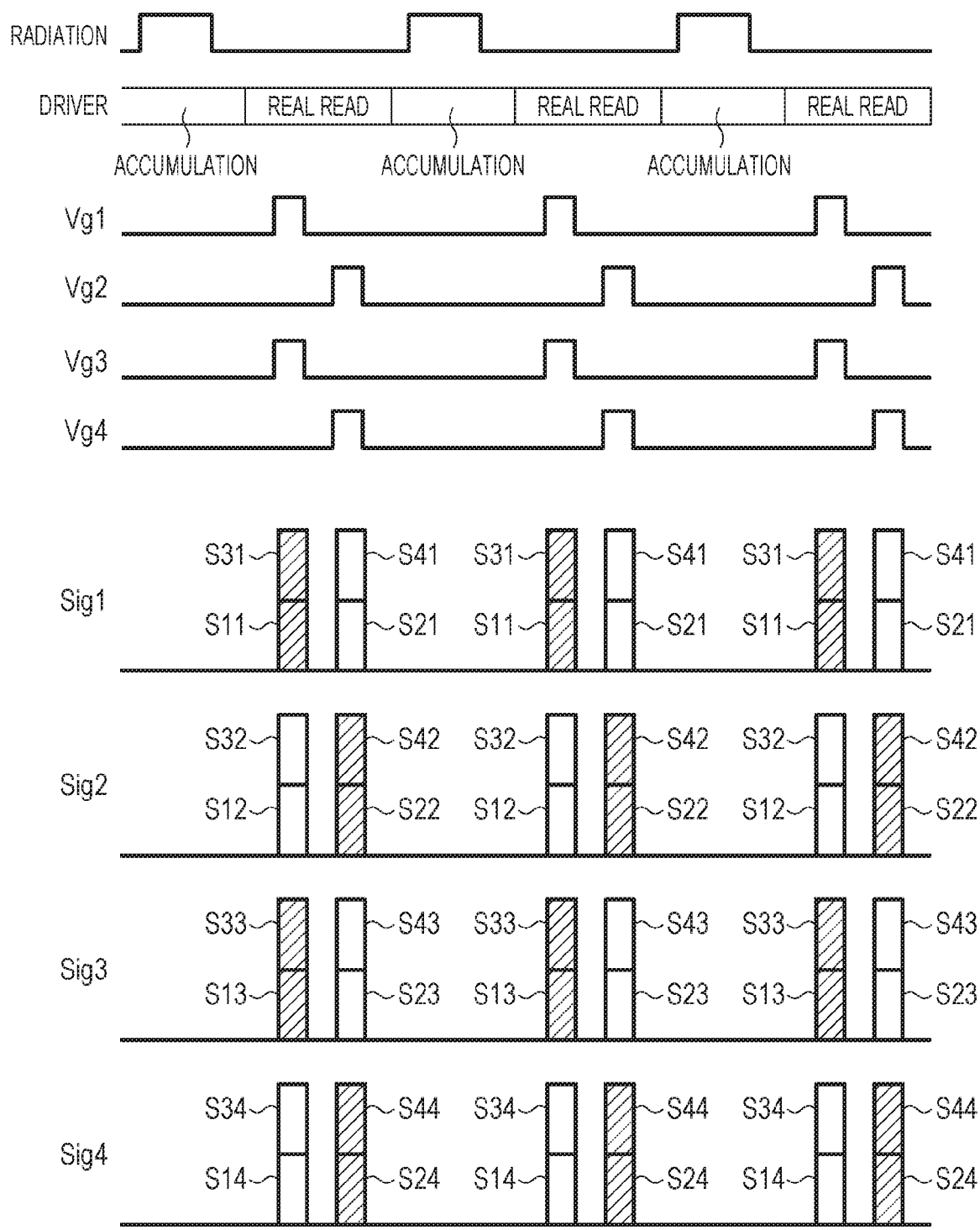
FIG. 6 is a timing chart illustrating the operation of the radiation image capturing apparatus in FIG. 1.

Drive for shooting a video will now be described with reference to FIG. 6. When a video is shot, the gate lines Vg are simultaneously driven at active levels for reading at a high rate. At this time, if the signals of the pixels PIX that include the first conversion elements 901 and the pixels PIX that include the second conversion elements 902 are outputted to a single column signal wiring line Sig, the energy components cannot be separated. Accordingly, as illustrated in FIG. 6, the gate signals that are supplied to the gate line Vg1 and the gate line Vg3 are simultaneously raised to active levels, and the signals of the conversion element S12 and the conversion element S32 that correspond to the first conversion elements 901 are outputted to the column signal line Sig2. Consequently, the signals of the conversion element S12 and the conversion element S32 are added (averaged) in the column signal line Sig2. At the same time, the signals of the conversion element S11 and the conversion element S31 that correspond to the second conversion elements 902 are outputted to the column signal line Sig1. Consequently, the signals of the conversion element S11 and the conversion element S31 are added (averaged) in the column signal line Sig1. The energy subtraction process can be performed by outputting the signals of the first conversion elements 901 and the second conversion elements 902 to the different column signal lines Sig.

Figure 10:
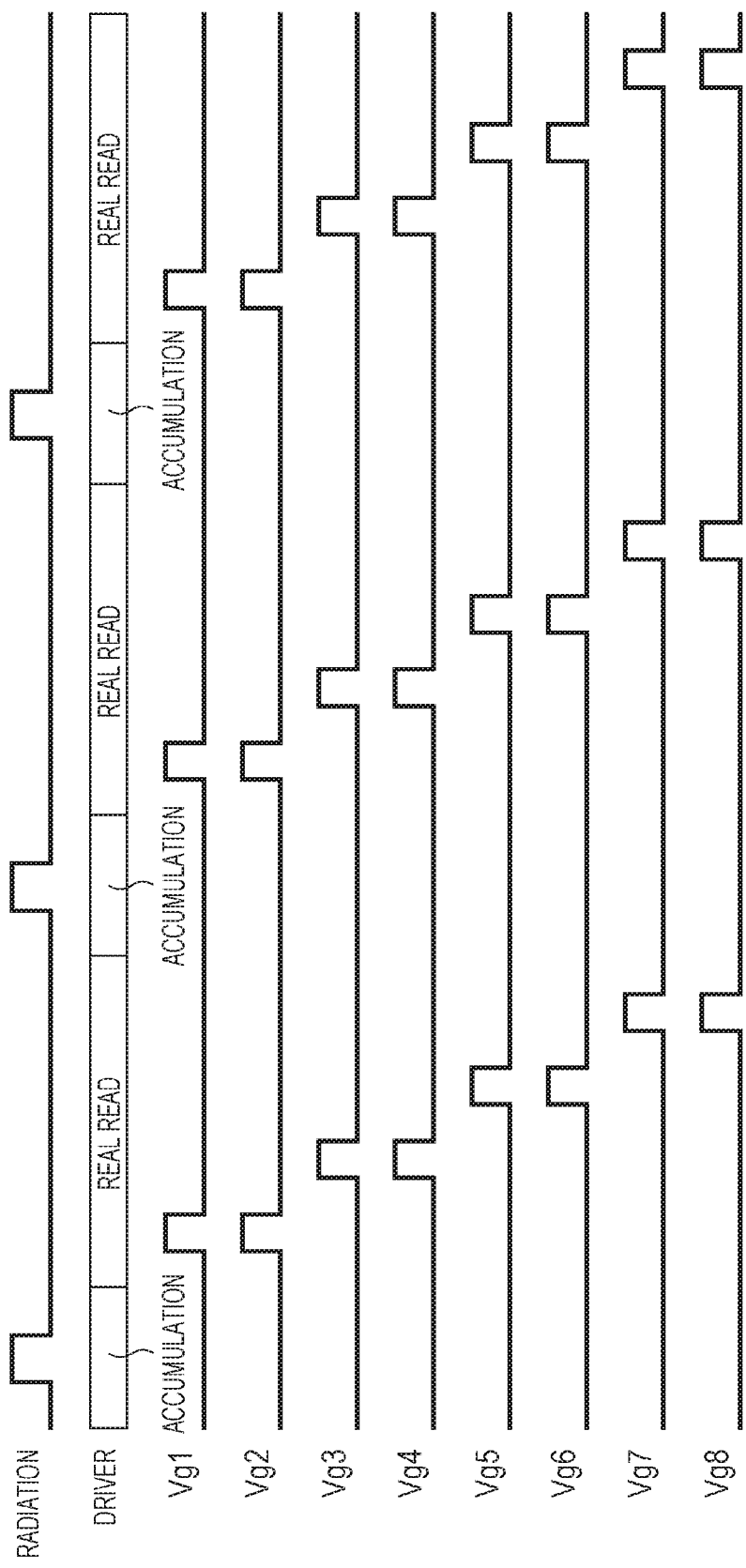
FIG. 10 is a timing chart illustrating the operation of the radiation image capturing apparatus in FIG. 9.

In the case of a drive method illustrated in FIG. 6, the gate line Vg1 and the gate line Vg3 are simultaneously raised to active levels for reading, and there is a space for one row therebetween. Accordingly, spatial resolution is reduced. In view of this, as illustrated in FIG. 9, the conversion elements S11, S22, S31, S42, S51, S62, S71, and S82 corresponding to the second conversion elements 902 are arranged such that the second conversion elements that are the subjects of addition are on a diagonal line of a matrix of 2 rows and 2 columns. The switches T11, T22, T31, T42, T51, T62, T71, and T82 are connected to the column signal line Sig1 in staggered arrangement. For such a structure, as illustrated in a timing chart in FIG. 10, the gate lines adjacent to each other, such as the gate line Vg1 and the gate line Vg2, are simultaneously (within the same period) raised to active levels. This enables the signals of the conversion elements S11 and the conversion elements S22 that correspond to the second conversion elements 902 to be added (averaged) in the column signal line Sig1.

Figure 11:
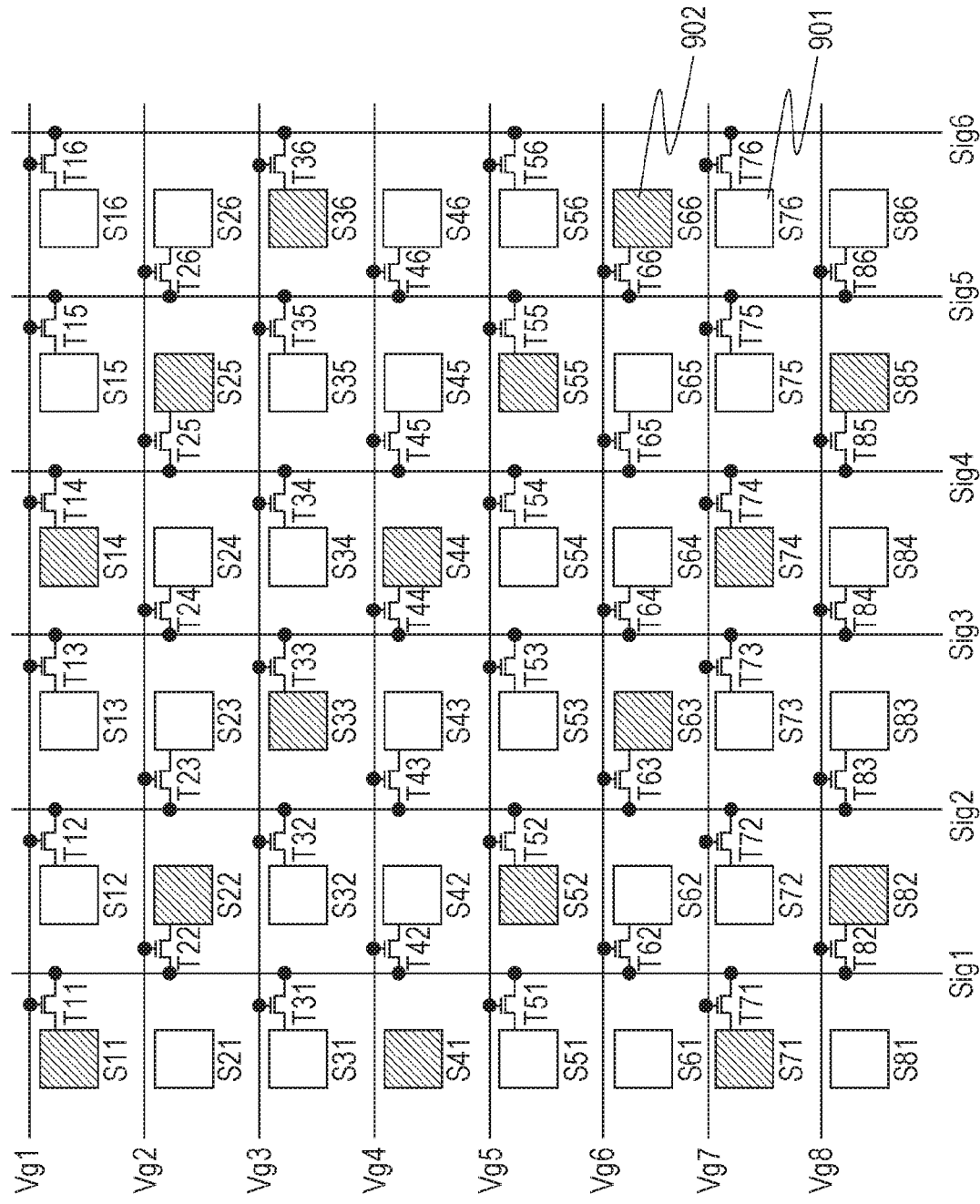
FIG. 11 illustrates an example of the structure of the image capturing panel of the radiation image capturing apparatus in FIG. 1.

Such features are not limited to the case where the ratio between the first conversion elements 901 and the second conversion elements 902 is one to one, that is, the density of arrangement of the first conversion elements 901 is 50%. For example, as illustrated in FIG. 11, the ratio between the first conversion elements 901 and the second conversion elements 902 is two to one, that is, the density of arrangement of the first conversion elements 901 is higher than the density of arrangement of the second conversion elements 902. Even in this case, when a video is shot, the resolution can be inhibited from being reduced, and reading at a high rate can be achieved in a manner in which the second conversion elements 902 in rows adjacent to each other are connected to the same column signal line Sig.

Figure 12:
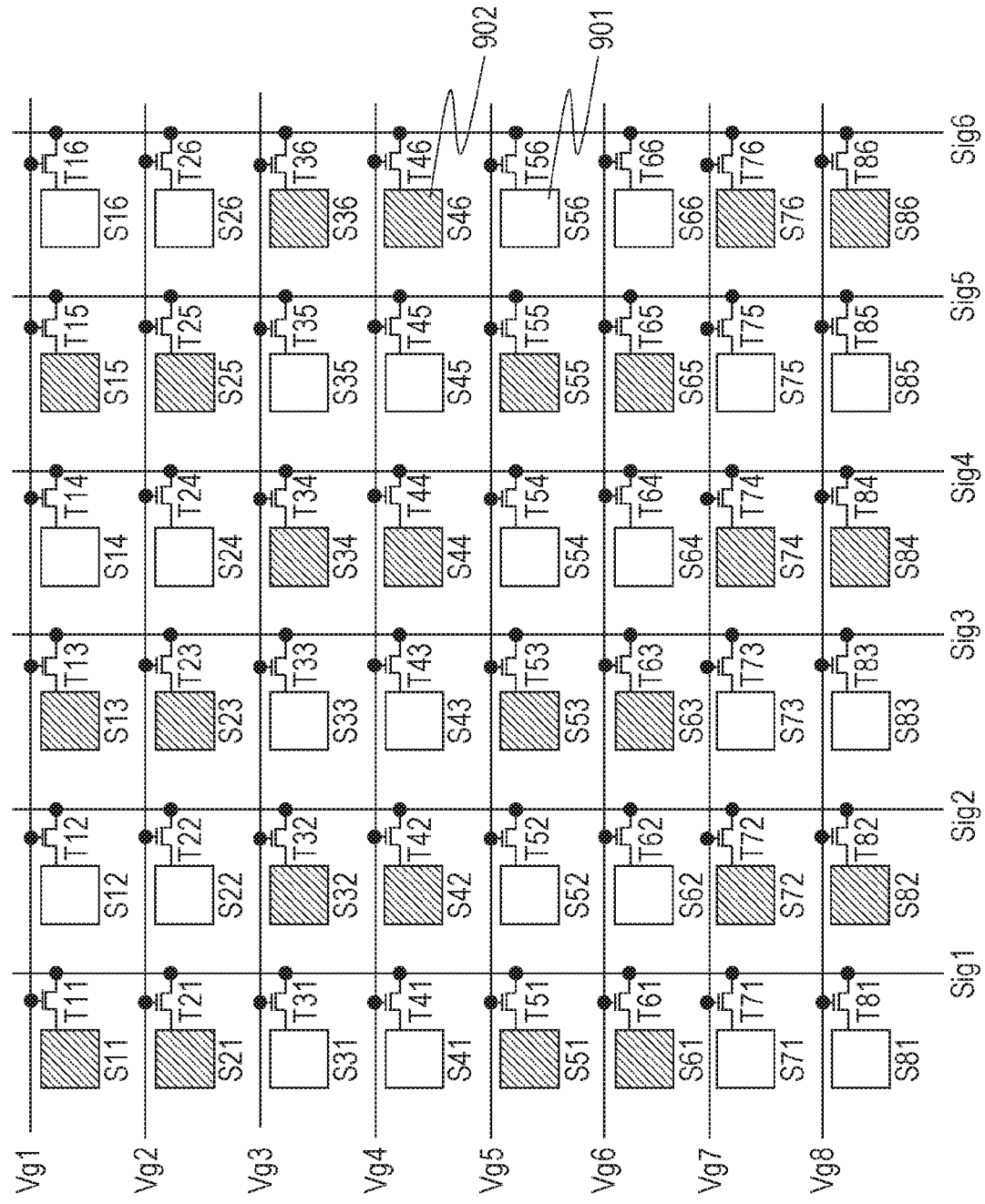
FIG. 12 illustrates an example of the structure of the image capturing panel of the radiation image capturing apparatus in FIG. 1.

As illustrated in FIG. 12, the addition (average) can be made in a manner in which the second conversion elements 902 that are the subjects of addition are continuously arranged in the column direction, and the signals of the second conversion elements 902 adjacent to each other are read out on the same column signal line Sig. Because of the addition (average), a readout rate when a video is shot is fast, and the resolution when the video is shot is sufficient. However, in the case where signals are separately read out from the second conversion elements 902 one by one when a still image is captured, the resolution in the row direction differs from the resolution in the column direction.

Figure 13:
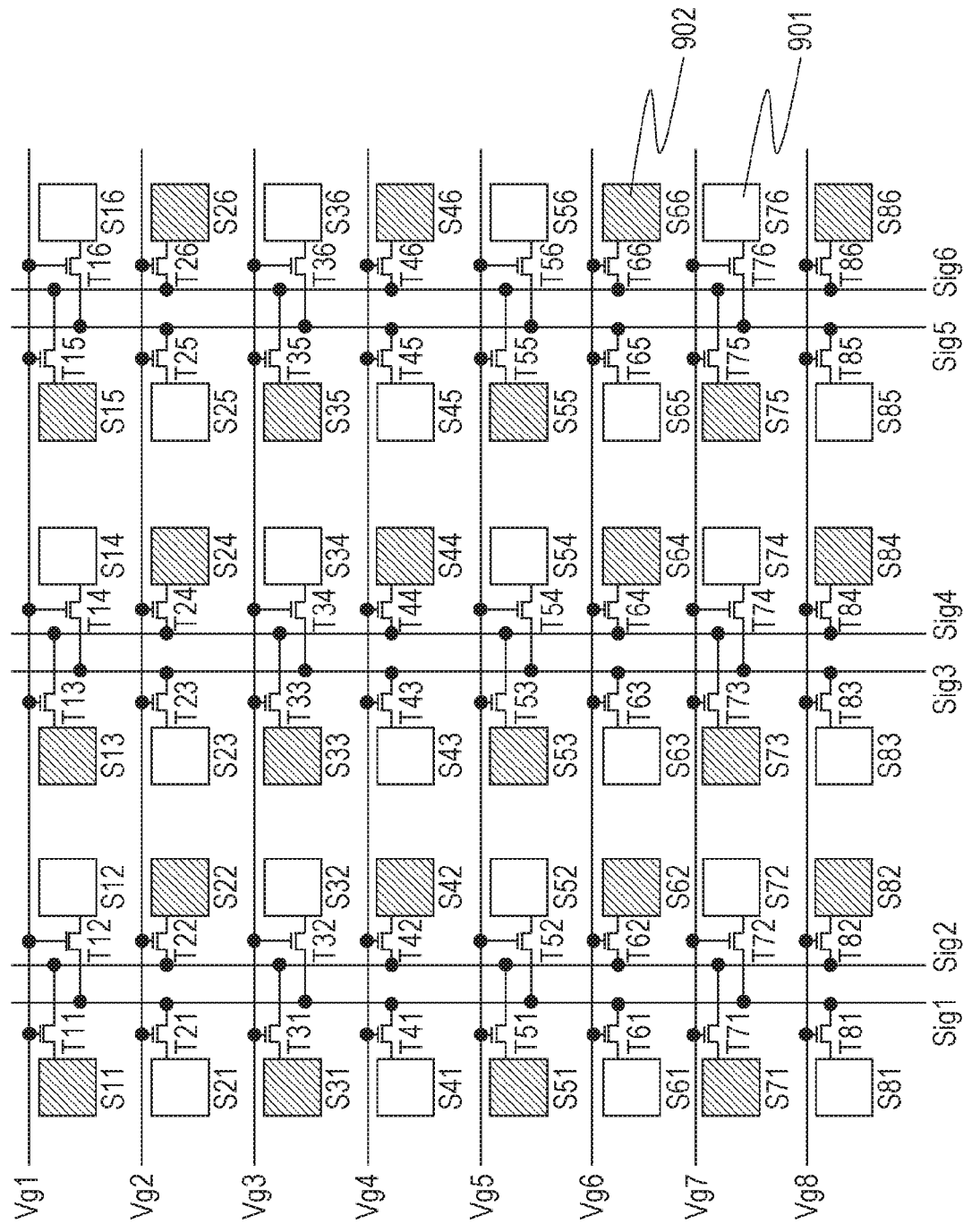
FIG. 13 illustrates an example of the structure of the image capturing panel of the radiation image capturing apparatus in FIG. 1.

The arrangement illustrated in FIG. 13 is also acceptable. In FIG. 13, the conversion elements S11, S22, S31, S42, S51, S62, S71, and S82 corresponding to the second conversion elements 902 are arranged such that the second conversion elements that are the subjects of addition are on a diagonal line of a matrix of 2 rows and 2 column. The switches T11, T22, T31, T42, T51, T62, T71, and T82 are connected to the column signal line Sig2 in staggered arrangement. The conversion elements S12, S21, S32, S41, S52, S61, S72, and S81 corresponding to the first conversion elements 901 are arranged such that the second conversion elements that are the subjects of addition are on a diagonal line of a matrix of 2 rows and 2 column. The switches T11, T22, T31, T42, T51, T62, T71, and T82 are connected to the column signal line Sig1 in staggered arrangement. The column signal line Sig1 and the column signal line Sig2 are located between the conversion elements in the first column and the conversion elements in the second column. In the case of a structure in FIG. 9, when the gate line Vg1 and the gate line Vg2 are simultaneously raised to active levels, the switch T13 and the switch T24 are turned on, and the signals of the conversion elements S13 and S24 are added. At the same time, the switches T12 and T23 are turned on, and the signals of the conversion elements S12 and S23 are added. When the signals are thus added, pixel centroids shift for a pair of the conversion elements S13 and S24 and a pair of the conversion elements S12 and S23. In some cases where the energy subtraction is performed by using an image having a shifted centroid, the resolution is reduced, and the artifact occurs. In the case of FIG. 13, the signals of the conversion elements S11 and S22 are added, and the signals of the conversion elements S12 and S21 are added. Accordingly, the pixel centroids match each other. Consequently, the resolution can be inhibited from being reduced, and an artifact can be inhibited from occurring.

The flow of image processing according to the present embodiment will now be described with reference to FIG. 7. At step S910, the control unit 214 first executes the dummy read described above and subsequently implements control to acquire the radiation image data such that electric charges that are produced by the conversion elements S are accumulated while the radiation is emitted. At step S911, the control unit 214 subsequently causes the drive circuit 114 and the readout circuit 113 to execute the real read to read out the radiation image data. At step S911, the radiation image data is outputted to the computer 240. At step S912, the control unit 214 subsequently performs an accumulation operation to acquire the offset image data. At step S913, the control unit 214 causes the drive circuit 114 and the readout circuit 113 to read out the offset image data and to outputs the offset image data to the computer 240.

The signal processing unit 241 of the computer 240 subsequently subtracts the offset image data that is acquired at step S913 from the radiation image data that is acquired at step S911 for offset correction. At step S915, the signal processing unit 241 subsequently separates the radiation image data after the offset correction into radiation image data that is outputted from the first conversion elements 901 and radiation image data that is outputted from the second conversion elements 902. In an example described herein, the radiation is incident on the structure in FIG. 3A from above in the figure, the light from the scintillator 904 is shielded, and the second conversion elements 902 receives light that is generated by high energy radiation from the scintillator 905. The radiation image data that is outputted from the first conversion elements 901 is referred to as double-sided image data. The radiation image data that is outputted from the second conversion elements 902 is referred to as single side image data.

At step S916, the signal processing unit 241 subsequently executes gain correction of the double-sided image data by using gain correction image data that is acquired in a state where there is no subject. At step S917, the signal processing unit 241 executes gain correction of the double-sided image data by using the gain correction image data.

After the gain correction, at step S918, the signal processing unit 241 executes pixel interpolation to interpolate lack of the double-sided image data of the pixels PIX that do not include the first conversion elements 901, in other words, the pixels PIX that include the second conversion elements 902. Similarly, at step S919, the signal processing unit 241 executes the pixel interpolation to interpolate lack of the single side image data of the pixels PIX that do not include the second conversion elements 902, in other words, the pixels PIX that include the first conversion elements 901. The pixel interpolation at steps S918 and S919 will be described with reference to FIG. 8A and FIG. 8B. The arrangement illustrated in FIG. 4B is taken as an example described herein, where the number of the pixels PIX that include the first conversion elements 901 is larger than the number of the pixels PIX that include the second conversion elements 902.

Figure 8A:
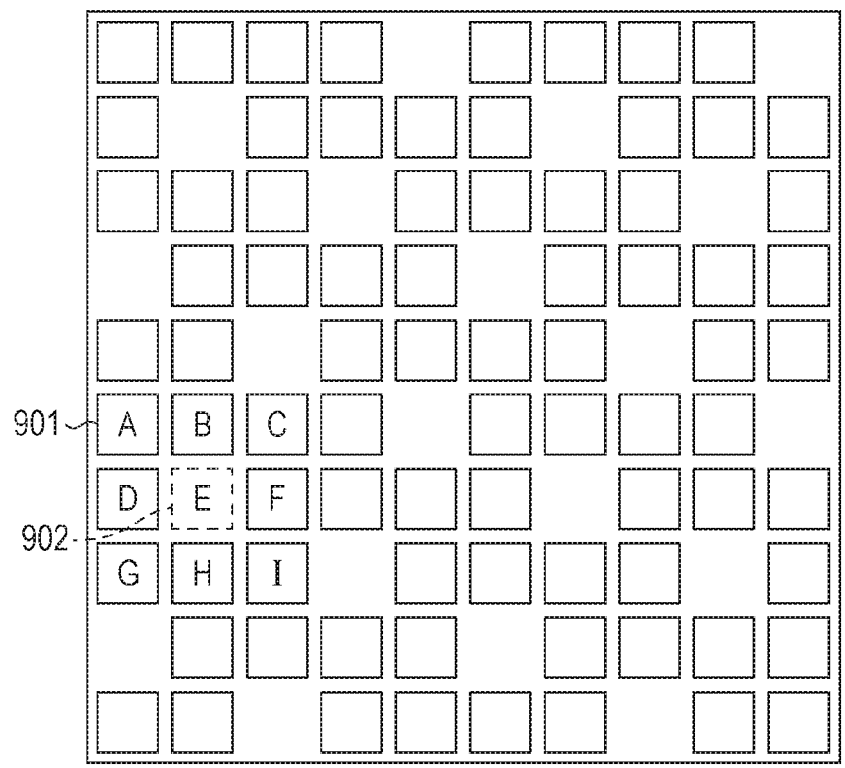
FIG. 8A illustrates an example of pixel interpolation of the radiation image capturing apparatus in FIG. 1.

The pixel interpolation of the double-sided image data will now be described with reference to FIG. 8A. The double-sided image data of a pixel E that includes the second conversion element 902 that outputs the single side image data is interpolated by using the double-sided image data of pixels A, B, C, D, F, G, H, and I that include the first conversion elements 901 that output the double-sided image data and that are adjacent to the pixel E. For example, the signal processing unit 241 may interpolate the double-sided image data of the pixel E by using the average value of the double-sided image data of eight pixels adjacent to the pixel E. For example, the signal processing unit 241 may interpolate the double-sided image data of the pixel E by using the average value of the double-sided image data of some pixels adjacent thereto such as the pixels B, D, F, and H. As a result of the pixel interpolation at step S918, the radiation image data is generated by using the high-energy component and the low-energy component of the radiation to the pixels PIX.

Figure 8B:
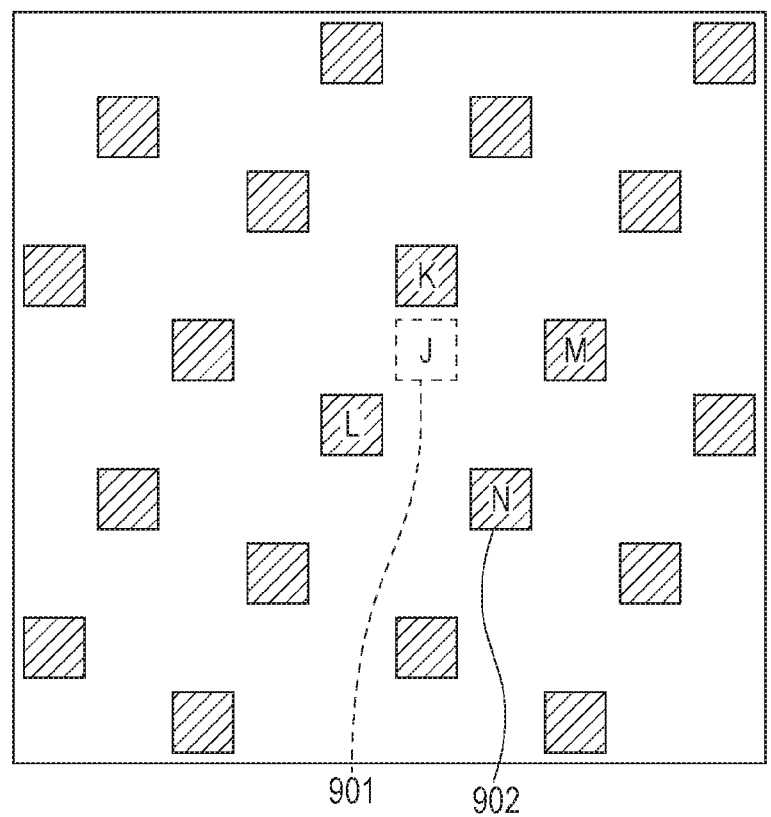
FIG. 8B illustrates an example of the pixel interpolation of the radiation image capturing apparatus in FIG. 1.

The pixel interpolation of the single side image data will now be described with reference to FIG. 8B. The single side image data of a pixel J that includes the first conversion element 901 that outputs the double-sided image data is interpolated by using the single side image data of pixels K, L, M, and N that include the second conversion elements 902 that output the single side image data and that are adjacent to the pixel J. For example, the signal processing unit 241 may interpolate the single side image data of the pixel J by using the average value of the single side image data of four pixels adjacent to the pixel J. In this case, for example, the distance from the position of the pixel J to the pixel K differs from the distance to the pixel N. Accordingly, the single side image data that is outputted from the pixels K, L, M, and N may be weighed depending on the distances for averaging. As a result of the pixel interpolation at step S919, the radiation image data is generated by using the high-energy component of the radiation to the pixels PIX.

At step S920, the signal processing unit 241 subsequently generates the radiation image data of the low-energy component of the radiation. In the case where each light shielding layer 903 is disposed near a position at which the radiation is incident on the second conversion element 902 as described above, the single side image data corresponds to the radiation image data of the high-energy component. The double-sided image data corresponds to the radiation image data having both of the high-energy and low-energy components. For this reason, the radiation image data of the low-energy component can be generated by subtracting the single side image data on which the pixel interpolation is executed from the double-sided image data on which the pixel interpolation is executed.

In the case where each light shielding layer 903 is disposed at the position opposite the position at which the radiation is incident on the second conversion element 902, the single side image data corresponds to the radiation image data of the low-energy component. For this reason, the radiation image data of the high-energy component can be generated by subtracting the single side image data on which the pixel interpolation is executed from the double-sided image data on which the pixel interpolation is executed. However, a radiation image of the high-energy component is an image of a radiation component that cannot be absorbed by the scintillator 904 near the position at which the radiation is incident. Accordingly, a light intensity from the scintillator 905 is less than a light intensity from the scintillator 904. Accordingly, in the case where the single side image data is subtracted from the double-sided image data to generate the radiation image data of the high-energy component, the radiation image data of the high-energy component contains noise of the radiation image data of the low-energy component. Consequently, the S/N ratio of the radiation image data of the high-energy component decreases. For this reason, according to the present invention, light from the position at which the radiation is incident on the second conversion elements 902 is shielded, the double-sided image data has the high-energy component and the low-energy component, and the single side image data has the high-energy component as described above. Subtracting the single side image data from the double-sided image data to generate a low-energy image improves the S/N ratio.

At step S922, the signal processing unit 241 generates the energy subtraction image. Specifically, the signal processing unit 241 acquires differences between the signals that are outputted from the first conversion elements 901 and the signals that are outputted from the second conversion elements 902, which are acquired at step S920, and differences between the signals that are outputted from the second conversion elements 902. Consequently, the energy subtraction image corresponding to a difference between the radiation image data of the high-energy component and the radiation image data of the low-energy component can be generated.

The signal processing unit 241 may generate a normal radiation image without the energy subtraction at step S920, based on the double-sided image data that is outputted from the first conversion elements 901 at step S918. The first conversion elements 901 receive the light from the scintillator 904 near the position at which the radiation is incident and the light from the scintillator 905 near the position opposite the position at which the radiation is incident. This enables the S/N ratio of the normal radiation image to be higher than that in the case where only light from a single scintillator is received.

What is considered herein is a radiation image capturing apparatus that is disclosed in Japanese Patent Application Laid-Open No. 2010-56396 and that includes two conversion elements one of which is a conversion element that receives only light from a scintillator near a position at which radiation is incident and the other of which is a conversion element that receives only light from a scintillator on the opposite side in order to generate a single piece of pixel data of a radiation image. A difference between two signals that are outputted from the two conversion elements is acquired to generate an energy subtraction image. A normal radiation image can be generated by adding the two signals. However, since the two conversion elements are needed to generate a single piece of the pixel data, a structure is complex, and there is a possibility that the manufacturing costs increase. In addition, the size of each conversion element decreases, and there is a possibility that the S/N ratio of an acquired signal decreases. When the normal radiation image is generated, and the two signals are added, noise that is superposed on the signals is also added, and there is a possibility that the S/N ratio decreases. According to the present embodiment, however, the light shielding layers 903 that shield the light from the scintillator 904 or the scintillator 905 are disposed only in some pixels PIX that include the second conversion elements 902 among the pixels PIX. That is, it is only necessary that the light shielding layers 903 are added to some of the pixels PIX. Accordingly, the structure is not complex, the manufacturing costs are reduced, and the radiation image capturing apparatus can acquire the energy subtraction image. The first conversion elements 901 receive the light that is emitted from the scintillator 904 and the scintillator 905, and sensitivity against the incident radiation is improved. Consequently, the quality of the acquired radiation image can be improved. When the normal radiation image is generated, the radiation image is generated from the signal that is generated by receiving the light that is emitted from the two scintillators 904 and 905. For this reason, the S/N ratio when the normal radiation image is captured is improved unlike the case of the structure disclosed in Japanese Patent Application Laid-Open No. 2010-56396.

According to the present embodiment, the radiation image of the radiation having two different energy components can be recorded by irradiating the subject with the radiation once (one shot method) by using the single image capturing panel 212. For this reason, the number of the components of the radiation image capturing apparatus decreases, and the manufacturing costs can be lower than that of a radiation image capturing apparatus that generates an energy subtraction image by using two image capturing panels. In addition, the weight of the radiation image capturing apparatus 210 can be decreased, and the radiation image capturing apparatus can be carried and easy to handle for a user. Since the energy subtraction image is generated by the single image capturing panel, the radiation image capturing apparatus does not have a problem in that conversion elements between two image capturing panels are not in position. Furthermore, the radiation image capturing apparatus can generate the normal radiation image having a high S/N ratio in addition to the energy subtraction image.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation image capturing apparatus comprising:
   a pixel array including a plurality of conversion elements arranged in a plurality of rows and a plurality of columns on an optically transparent substrate;
   a plurality of signal lines that outputs a signal generated by the plurality of conversion elements and that extends in a column direction;
   a first scintillator disposed so as to cover a first surface of the substrate; and
   a second scintillator disposed so as to cover a second surface of the substrate opposite the first surface,
   wherein the plurality of conversion elements includes a plurality of first conversion elements and a plurality of second conversion elements,
   wherein a light shielding layer is disposed between the first scintillator and the plurality of second conversion elements such that an amount of light that is received by the plurality of second conversion elements from the first scintillator is smaller than that received by the plurality of first conversion elements, and
   wherein a number of columns of the plurality of conversion elements is equal to a number of the plurality of signal lines.

2. The radiation image capturing apparatus according to claim 1, wherein a second conversion element in a row adjacent to one second conversion element among the plurality of second conversion elements is connected to a signal line to which the one second conversion element is connected among the plurality of signal lines.

3. The radiation image capturing apparatus according to claim 2, further comprising: a drive circuit that drives the pixel array, wherein the drive circuit drives the pixel array such that a signal from the one second conversion element and a signal from the second conversion element in the adjacent row are outputted to the signal line within the same period.

4. The radiation image capturing apparatus according to claim 1,
   wherein the plurality of first conversion elements receive light from the first scintillator and the second scintillator,
   wherein the plurality of second conversion elements receive light from the second scintillator, and
   wherein the plurality of conversion elements is disposed between the first surface and the first scintillator.

5. The radiation image capturing apparatus according to claim 4,
wherein the plurality of conversion elements includes a first electrode, a semiconductor layer, and a second electrode in this order in a direction from the first surface toward the first scintillator, and
wherein the second electrode functions as the light shielding layer for the plurality of second conversion elements.

6. The radiation image capturing apparatus according to claim 4, wherein an anti-scattering layer is disposed between the second scintillator and the second surface.

7. The radiation image capturing apparatus according to claim 1, wherein the plurality of conversion elements is disposed between the second surface and the second scintillator.

8. The radiation image capturing apparatus according to claim 7,
wherein the plurality of conversion elements includes a first electrode, a semiconductor layer, and a second electrode in this order in a direction from the second surface toward the second scintillator, and
wherein the first electrode functions as the light shielding layer for the plurality of second conversion elements.

9. The radiation image capturing apparatus according to claim 1, wherein radiation enters from the first surface.

10. The radiation image capturing apparatus according to claim 1, wherein radiation enters from the second surface.

11. The radiation image capturing apparatus according to claim 1, wherein conversion elements arranged in a row direction that intersects the column direction among the plurality of conversion elements include the same number of second conversion elements in each row.

12. The radiation image capturing apparatus according to claim 11, wherein conversion elements arranged in the column direction among the plurality of conversion elements include the same number of second conversion elements in each column.

13. The radiation image capturing apparatus according to claim 1, wherein conversion elements arranged in the column direction among the plurality of conversion elements include the same number of second conversion elements in each column.

14. The radiation image capturing apparatus according to claim 1, wherein a number of the plurality of second conversion elements is smaller than a number of the plurality of first conversion elements.

15. A radiation image capturing system comprising:
the radiation image capturing apparatus according to claim 1; and
a signal processing unit that processes a signal from the radiation image capturing apparatus.

16. The radiation image capturing system according to claim 15, wherein the signal processing unit generates an energy subtraction image based on a signal that is outputted from the plurality of first conversion elements and a signal that is outputted from the plurality of second conversion elements.

17. The radiation image capturing system according to claim 15, wherein the signal processing unit generates the energy subtraction image based on a difference between the signal that is outputted from the plurality of first conversion elements and the signal that is outputted from the plurality of second conversion elements, and a difference between signals that are outputted from the plurality of second conversion elements.

18. The radiation image capturing system according to claim 15, wherein the signal processing unit generates a normal radiation image based on a signal that is outputted from the plurality of first conversion elements.

19. A radiation image capturing apparatus comprising:
a first scintillator;
a second scintillator;
a pixel array including a plurality of conversion elements arranged in a plurality of rows and a plurality of columns on an optically transparent substrate arranged between the first scintillator and the second scintillator; and
a plurality of signal lines that outputs a signal generated by the plurality of conversion elements and that extends in a column direction,
wherein the plurality of conversion elements includes a plurality of first conversion elements and a plurality of second conversion elements,
wherein a light shielding layer is disposed between the first scintillator and the plurality of second conversion elements such that an amount of light that is received by the plurality of second conversion elements from the first scintillator is smaller than that received by the plurality of first conversion elements, and
wherein a number of columns of the plurality of conversion elements is equal to a number of plurality of signal lines.

20. A radiation image capturing system comprising:
the radiation image capturing apparatus according to claim 19; and
a signal processing unit that processes a signal from the radiation image capturing apparatus.

* * * * *